(12) United States Patent
Easley et al.

(10) Patent No.: US 8,512,340 B2
(45) Date of Patent: Aug. 20, 2013

(54) TORSIONAL PINEAPPLE DISSECTION TIP

(75) Inventors: James C. Easley, St. Charles, MO (US);
Edward J. Timm, Wildwood, MO (US);
Robert F. Spetzler, Paradise Valley, AZ (US)

(73) Assignee: Stryker Corporation, Kalamazoo, MI (US)

( * ) Notice: Subject to any disclaimer, the term of this patent is extended or adjusted under 35 U.S.C. 154(b) by 1911 days.

(21) Appl. No.: 11/174,046

(22) Filed: Jul. 1, 2005

(65) Prior Publication Data
US 2006/0004396 A1 Jan. 5, 2006

Related U.S. Application Data

(60) Provisional application No. 60/584,978, filed on Jul. 2, 2004.

(51) Int. Cl.
*A61B 17/00* (2006.01)
(52) U.S. Cl.
USPC .......................................................... 606/79
(58) Field of Classification Search
USPC .................... 606/79–80, 167–171
See application file for complete search history.

(56) References Cited

U.S. PATENT DOCUMENTS

| | | | | |
|---|---|---|---|---|
| 3,667,470 A | * | 6/1972 | Rubin | 606/84 |
| 3,945,375 A | * | 3/1976 | Banko | 600/104 |
| 4,177,952 A | * | 12/1979 | Rikker | 241/40 |
| 4,188,952 A | * | 2/1980 | Loschilov et al. | 606/79 |
| 4,243,048 A | * | 1/1981 | Griffin | 600/564 |
| 4,265,231 A | * | 5/1981 | Scheller et al. | 606/80 |
| 4,541,423 A | * | 9/1985 | Barber | 606/80 |
| 4,572,753 A | * | 2/1986 | Bach | 156/73.1 |
| 4,625,725 A | * | 12/1986 | Davison et al. | 606/85 |
| 4,646,736 A | * | 3/1987 | Auth | 606/159 |
| 4,646,738 A | * | 3/1987 | Trott | 606/170 |
| 4,647,325 A | * | 3/1987 | Bach | 156/73.1 |
| 4,663,556 A | * | 5/1987 | Kumada | 310/333 |
| 4,706,659 A | * | 11/1987 | Matthews et al. | 606/80 |
| 4,751,922 A | * | 6/1988 | DiPietropolo | 606/80 |
| 4,920,954 A | * | 5/1990 | Alliger et al. | 606/128 |
| 5,051,647 A | * | 9/1991 | Uchikawa et al. | 310/323.12 |
| 5,152,744 A | * | 10/1992 | Krause et al. | 604/22 |
| 5,304,115 A | * | 4/1994 | Pflueger et al. | 604/22 |
| 5,318,570 A | * | 6/1994 | Hood et al. | 606/99 |
| 5,342,365 A | * | 8/1994 | Waldman | 606/85 |
| 5,346,502 A | * | 9/1994 | Estabrook et al. | 606/169 |
| 5,358,505 A | * | 10/1994 | Wuchinich | 606/99 |
| 5,372,138 A | * | 12/1994 | Crowley et al. | 600/463 |
| 5,540,693 A | * | 7/1996 | Fisher | 606/79 |
| 5,833,692 A | * | 11/1998 | Cesarini et al. | 606/79 |
| 5,854,529 A | * | 12/1998 | Ashizawa et al. | 310/323.01 |
| 5,891,149 A | * | 4/1999 | Young et al. | 606/80 |
| 5,935,131 A | * | 8/1999 | Bonutti | 606/80 |
| 5,968,048 A | * | 10/1999 | Harder | 606/80 |

(Continued)

*Primary Examiner* — Mary Hoffman
(74) *Attorney, Agent, or Firm* — Howard & Howard Attorneys PLLC (57) ABSTRACT

A torsional dissection tip and method of use comprising a longitudinal-torsional resonator having a cutting surface at a distal end with cutting teeth of a pitch optimized to the torsional or longitudinal displacement of the distal tip. The present art apparatus and method of use utilizes uniquely designed cutting surface geometries with the aforesaid pitch attributes for surgical applications. Utilization of the present art torsional dissection tip allows a surgeon to easily remove hard tissues such as bone without moving the present art instrument to any site except that which is to be dissected.

12 Claims, 12 Drawing Sheets

(56) References Cited

U.S. PATENT DOCUMENTS

| | | | |
|---|---|---|---|
| 6,077,285 A * | 6/2000 | Boukhny | 606/169 |
| 6,174,313 B1 * | 1/2001 | Bonutti | 606/80 |
| 6,402,769 B1 * | 6/2002 | Boukhny | 606/169 |
| RE38,018 E * | 3/2003 | Anctil et al. | 606/170 |
| 6,723,110 B2 * | 4/2004 | Timm et al. | 606/169 |
| 6,910,889 B1 * | 6/2005 | Hickok | 433/119 |
| 6,984,220 B2 * | 1/2006 | Wuchinich | 604/22 |
| 7,374,552 B2 * | 5/2008 | Wuchinich | 604/22 |
| 2001/0047166 A1 * | 11/2001 | Wuchinich | 606/1 |
| 2002/0151825 A1 * | 10/2002 | Rubenchik et al. | 601/2 |
| 2002/0156492 A1 * | 10/2002 | Timm et al. | 606/169 |
| 2004/0023187 A1 * | 2/2004 | Hickok | 433/119 |
| 2005/0177184 A1 * | 8/2005 | Easley | 606/167 |
| 2005/0264139 A1 * | 12/2005 | Wuchinich | 310/333 |
| 2005/0277869 A1 * | 12/2005 | Boukhny | 604/22 |
| 2008/0103418 A1 * | 5/2008 | Wuchinich | 601/2 |

* cited by examiner

TORSIONAL PINEAPPLE DISSECTION TIP

This application claims priority of U.S. Provisional Patent Application No. 60/584,978, filed Jul. 2, 2004 entitled Torsional Pineapple Dissection Tip.

BACKGROUND OF THE INVENTION

The art of the present invention relates to torsional dissection tips in general and more particularly to a tip for a linear or longitudinal ultrasonic generator which provides uniquely patterned and formed teeth which are able to uniquely provide torsional and linear dissection of hard or dense biological tissues including intracranial bone. The present art embodiments utilize a unique substantially pineapple shaped head. The art of the present invention is especially suited for dissection of bone and calcified neoplasm during neurosurgery, spinal surgery, orthopedic surgery, plastic/reconstructive surgery, and ear, nose, and throat surgery without the deleterious effects to nearby tissues presented with high speed drilling.

The prior art describes a longitudinal-torsional ultrasonic tissue dissection apparatus in U.S. application No. 09/833,109 filed Apr. 11, 2001 by Wuchinich, entitled Longitudinal-Torsional Ultrasonic Tissue Dissection published Nov. 29, 2001 with U.S. publication number 2001/0047166 A1. The aforesaid prior art describes an apparatus for providing torsional movement from a longitudinal ultrasonic generator but fails to provide optimum cutting teeth or head design for hard or dense biological tissues. The prior art utilizes a series of pyramidal shaped teeth spaced apart many times the torsional and/or linear cutting displacement. The aforesaid art is only marginally effective for the intended application. The present art provides a plurality of optimally spaced teeth with a pitch corresponding to a torsional and/or longitudinal stroke of the torsional ultrasonic generator. The present art embodiments provide the aforesaid with an expanded head with pyramidal projections located circumferentially around the distal shaft orifice.

During many surgical procedures, it is necessary to remove all or a portion of a bony structure in order to provide access to other tissue or organs. In other instances it becomes necessary to shape bone to facilitate approximation of implants, autologous materials, wound closure, etc. Often the shaping or removal of the bony material is done in close proximity to fragile and/or eloquent tissues. In these instances it is desirable that the instrument used for bone removal act in a manner that is predictable and precise. Specific requirements would include, but not be limited to minimization of torque at start up to prevent displacement of the instrument from intended tissue contact, minimized, precise, and discrete tissue impact to restrict alternate site injury potentially caused by the transmitted effect of the instrument, and an overall action that allows the surgeon to focus upon the area of interest rather than having to be concerned with complications secondary to the use of the instrument.

Much of the current state of the art as it relates to these applications is found in the employment of high-speed air motors or drills. Reaching rotational speeds of up to 95,000 rpm, burrs attached to the air motor affect removal of tissue at varied rates, dependent upon the surface of the burr. Hardened steel cutting tools remove bone rapidly and diamond coated tools affect removal at a much slower rate, but do so with a greater deal of forgiveness, as there is some degree of discrimination in the diamond means of tissue destruction. The spinning burr is directed against the bone to be removed and the cutting surface cuts or grinds it away. A disadvantage of the high-speed burr is a tendency to "skip" from the bone upon initial contact or displacement of the handpiece in the direction of rotation as it contacts the surface to be removed. Due to the constant rotation of the burr, surrounding tissue and/or materials, e.g. sutures, surgical patties, etc., can be inadvertently captured by the rotating shaft of the instrument, thus pulling the tissue and/or materials around the shaft in a "spooling" action. In the case of diamond coated burrs, clearance of chips from the operative site is minimized, thereby trapping the associated heat generated by contact between the tool and the bone. As such, excessive heat generation is a genuine concern, with temperatures in excess of 180 degrees Fahrenheit having been clinically documented. As the generally accepted heat threshold for the inducement of neuronal injury is approximately 109 degrees Fahrenheit, the heat generated by a diamond tool on a high-speed air motor constitutes a genuine clinical concern.

As aforesaid, recently a means of accomplishing the aforesaid objectives has become commercially available as described in the Wuchinich application. This instrument consists of an ultrasonic motor or generator connected to a shaped tip. The motor is designed to vibrate longitudinally (along its axis), at a fixed frequency with variable amplitude. The tip is designed to convert the longitudinal vibration to a combination of longitudinal and torsional vibration. The aforesaid art teaches how to make an instrument that incorporates longitudinal-torsional motion and how this tip might then be applied to tissue. It does not describe potential tip geometry or configuration that may or may not be advantageous.

Commercially available embodiments of the aforesaid art utilize a working surface having a plurality of teeth or grooves spaced substantially greater than the torsional and/or linear cutting displacement rather than distinct substantially pyramid shaped teeth which are spaced two times or less than the aforesaid displacement. The present art utilizes a plurality of pyramid or tetrahedral shaped teeth arrayed on the working surface which are spaced in all embodiments at least two times or less than the maximum aforesaid displacement.

Accordingly, it is an object of the present invention to provide a torsional dissection tip having a plurality of optimally spaced teeth with a pitch corresponding to a torsional and/or longitudinal stroke of the torsional ultrasonic generator.

Another object of the present invention is to provide a torsional dissection tip having a plurality of optimally spaced teeth, at least two times or less than the longitudinal or torsional tool surface displacement, which may take many different forms, including but not limited to pyramid or tetrahedral shapes, yet function optimally.

SUMMARY OF THE INVENTION

To accomplish the foregoing and other objects of this invention there is provided a torsional dissection tip for use with an ultrasonic motor. The apparatus is especially suited for use with and during orthopedic surgery. As aforesaid, the present art utilizes a plurality of pyramid, tetrahedral, or other shaped teeth arrayed on the working or cutting surface which are spaced in all embodiments at least two times or less than the maximum aforesaid displacement. (i.e. amplitude)

For the preferred embodiment, tooth pitch, i.e. distance between successive teeth, is 0.3 or 1 mm, but may comprise any length provided the aforesaid criteria are met. Alternative embodiments of the present art may utilize any type of teeth with a pitch which is substantially optimum for the torsional or longitudinal displacement. For the present and prior art, torsional vibration displacement is typically 300 microns (0.3 mm), with the ratio of longitudinal to torsional displacement regulated by the construction of the tip. While commercially available embodiments of the prior art, such as available from Miwatec of Kawasaki Japan, are capable of accomplishing the clinical objective of bone removal, said prior art requires constant motion of the instrument tip to avoid excessive heat generation, tissue necrosis, and neuronal injury. It is theorized that this excessive heat generation is caused by bone rubbing the sides of the grooves as opposed to the tips of the grooves. That is, the instrument tip typically has both longitudinal and torsional movement and said longitudinal movement is substantially parallel with the prior art grooves. This longitudinal movement when utilized with the prior art does not remove tissue but simply heats said tissue. This excessive heat generation is avoided in the present art via utilization of said plurality of pyramid shaped teeth with the aforesaid optimum spacing.

The present art invention comprises a longitudinal-torsional resonator (L-T resonator) having a cutting surface tip comprising a plurality of teeth arranged with a pitch, i.e. distance between successive teeth in a plane of motion, substantially equal to the torsional displacement of said tip. Said L-T resonator has a first or proximal end having a preferably female threaded portion which connects with an ultrasonic generator or electromechanical transducer and a second or distal end having said cutting surface plane. A central axis of said L-T resonator is centrally located and extends from said first end to said second end. In a preferred embodiment, a tubular aspiration and/or irrigation path extends from said threaded portion through said second end with an approximate 0.059 inch diameter and forms an orifice at said second or distal end. Alternative embodiments may utilize a plurality of irrigation path diameters. Also in a preferred form, from said first end to said second end said L-T resonator tapers in step form with preferably three steps. Alternative embodiments may utilize any number of steps or simply taper said L-T resonator and further use numerous first end connecting methods recognized within the art including but not limited to screw threads, pins, press fits, welding, brazing or the connection may be metallurgically continuous with the ultrasonic generator. Said ultrasonic generator or electro-mechanical transducer is described in the prior art and is only referenced herein as it interfaces with the present invention.

As described within the prior art, within the body of said L-T resonator is a cross sectional mass which is inhomogeneous. Said inhomogeneous section may take the form of twisting a flat bar or grooving a round one, i.e. spiraling grooves around the circumference, or varying the density or elasticity of the bar in a helical manner. This inhomogeneity should preferentially be made in the portion of the bar subjected to maximum stress. When the aforesaid inhomogeneity is introduced, longitudinal motion of the ultrasonic generator is at least partially converted into torsional motion at the working surface or distal tip. In the preferred embodiment, said inhomogeneity comprises a plurality of helical grooves within the second step of the L-T resonator.

In an prior art embodiment, said cutting surface plane is positioned substantially tangential and away from the outside diameter of the L-T resonator at said second end. That is, said surface is preferably positioned on a short arm at said second end away from the outer diameter or circumference of said L-T resonator. Preferably said cutting surface is planar or has a radius which substantially conforms to the radius from the central axis of the L-T resonator to the cutting surface. A preferred embodiment of the present art cutting surface is preferably positioned substantially tangential and parallel in at least a 180 degree arc and away from the outside diameter of the L-T resonator at said second end. That is, said surface is preferably positioned on a short substantially circular arm or projection at said second end away from the outer diameter or circumference of said L-T resonator. Preferably said preferred embodiment cutting surface has a tapered radius or tapered surface relative to the central axis of the L-T resonator whereby said cutting surface forms a partial conical surface with the smallest radius of said conical surface at the second or distal end. As shown in the figures, the present art uniquely incorporates a plurality of cutting teeth on said cutting surface which, unlike the prior art, are capable of cutting hard tissue both longitudinally and torsionally. In the form described, each of said teeth substantially come to a point maximally away from said central axis. In a preferred form, said teeth are pyramidal or tetrahedral in shape and uniformly positioned onto said cutting surface. Said teeth may take substantially one dimensional triangular or rectangular, cubical, or other tetrahedral, pentahedral, or pyramidal forms with any number of surfaces in alternative embodiments without departing from the scope of the present art.

The present art invention allows the efficient removal of bone with torsional or longitudinal motion of the instrument tip. The device may be applied to ultrasonic motors that vibrate longitudinally, in torsion, or a combination of both longitudinal and torsional motion. That is, unlike grooves of the prior art, the present art plurality of teeth will remove dense tissues when motion is applied in any two dimensional direction along the plane of the plurality of teeth.

The vibration amplitude or displacement at the working surface is typically approximately 300 microns (0.3 mm) and the tooth pitch is, in a preferred embodiment, substantially equal to said vibration amplitude. The shape of the teeth and array pattern may take many forms provided the working surface provides a plurality of teeth. For alternative embodiments, the tooth pitch should be no greater than two times the vibration amplitude and as aforesaid, in a preferred form, be equal to or less than the vibration amplitude. This allows the path swept by the vibrating teeth to coincide or overlap with the path of the adjacent tooth. In this manner bone is removed along the entire working surface of the tip, disallowing the entrapment of the heat by the intimate contact of the sides of the teeth with the bone. As such, heat generation is minimized, bone removal is maximized, and deleterious secondary effects are eliminated.

The art of the present invention may be manufactured from a plurality of materials having the elastic and hardness properties desired, including but not limited to titanium alloys, commercially pure titanium, and super-elastic alloys such as nitinol. The present art may further utilize anti-reflective surface treatments, coatings, or processes to optimize operation.

BRIEF DESCRIPTION OF THE DRAWINGS

Numerous other objects, features and advantages of the invention should now become apparent upon a reading of the following detailed description taken in conjunction with the accompanying drawings, in which.

DETAILED DESCRIPTION

Figure 1:
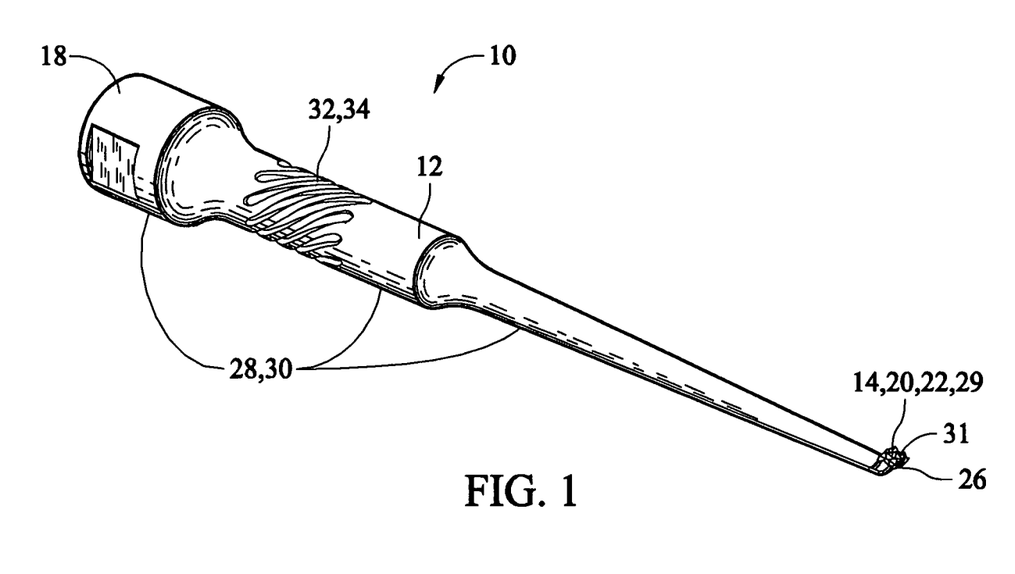
FIG. 1 is a left side perspective view of a prior art embodiment of the torsional dissection tip which is substantially symmetric with a right side perspective view.
Figure 2:
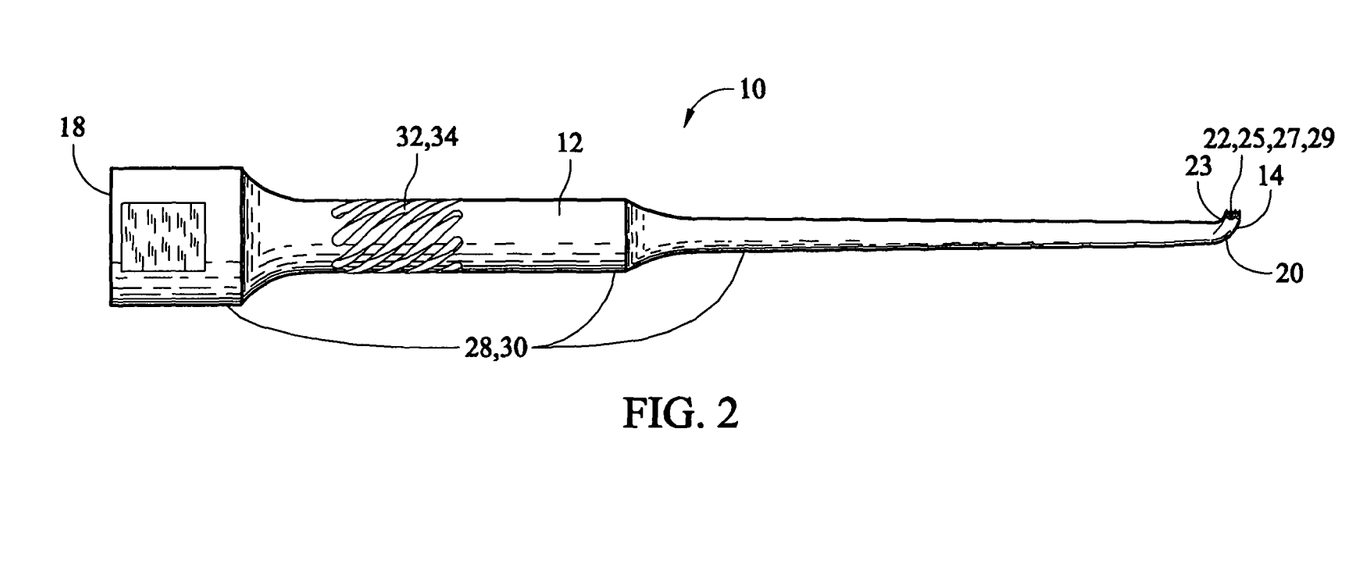
FIG. 2 is a left side plan view thereof which is substantially symmetric with a right side plan view.
Figure 3:
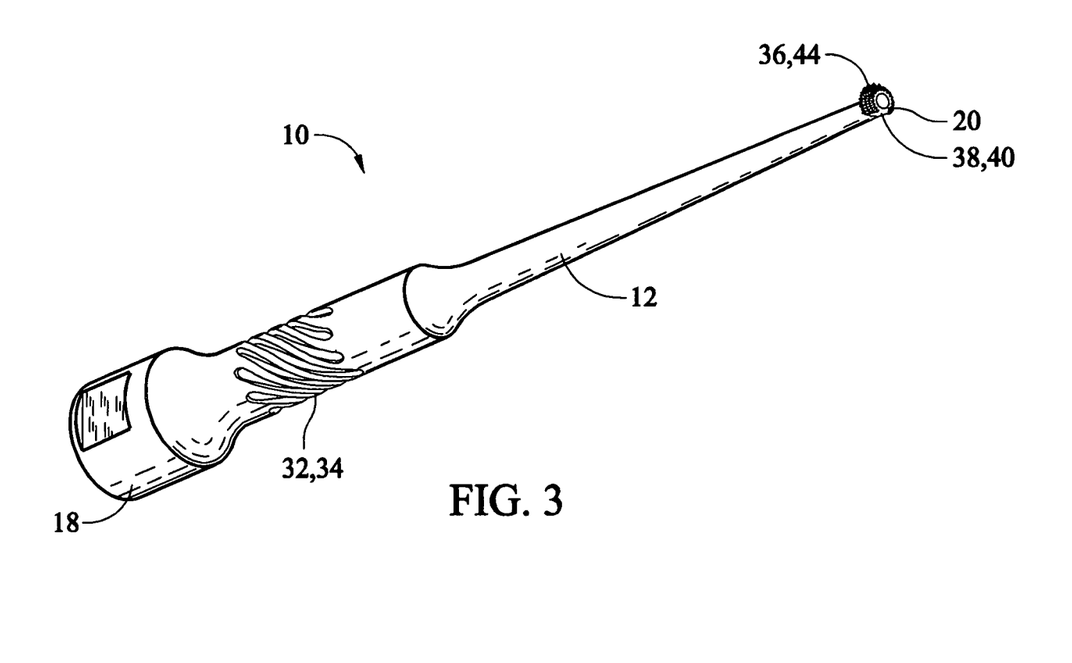
FIG. 3 is a left side perspective view of a preferred embodiment of the torsional pineapple dissection tip which is substantially symmetric with a right side perspective view.
Figure 4:
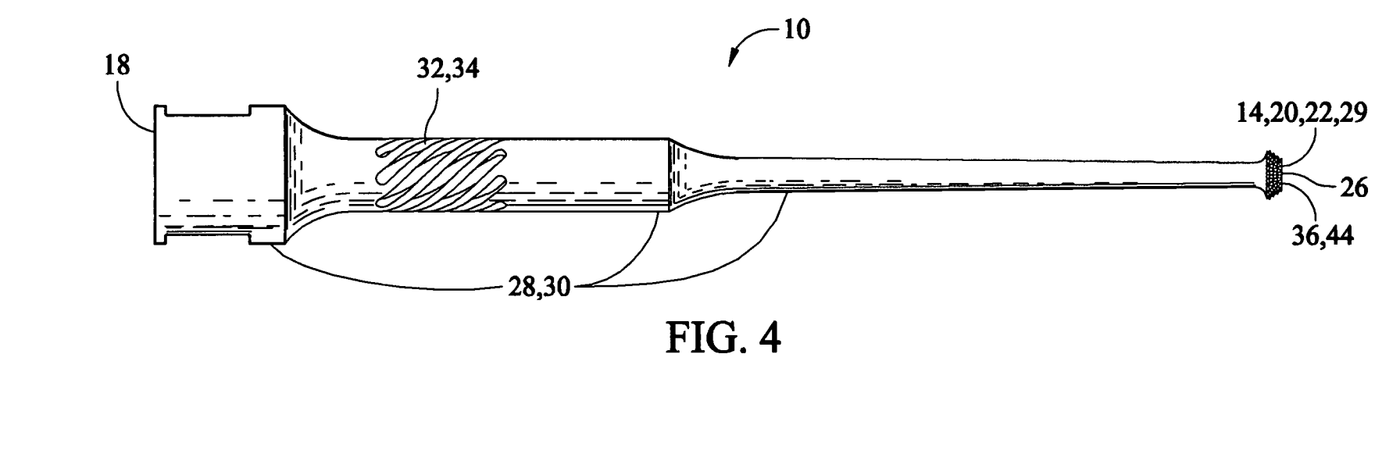
FIG. 4 is a top side plan view of a preferred embodiment of the torsional dissection tip.
Figure 5:
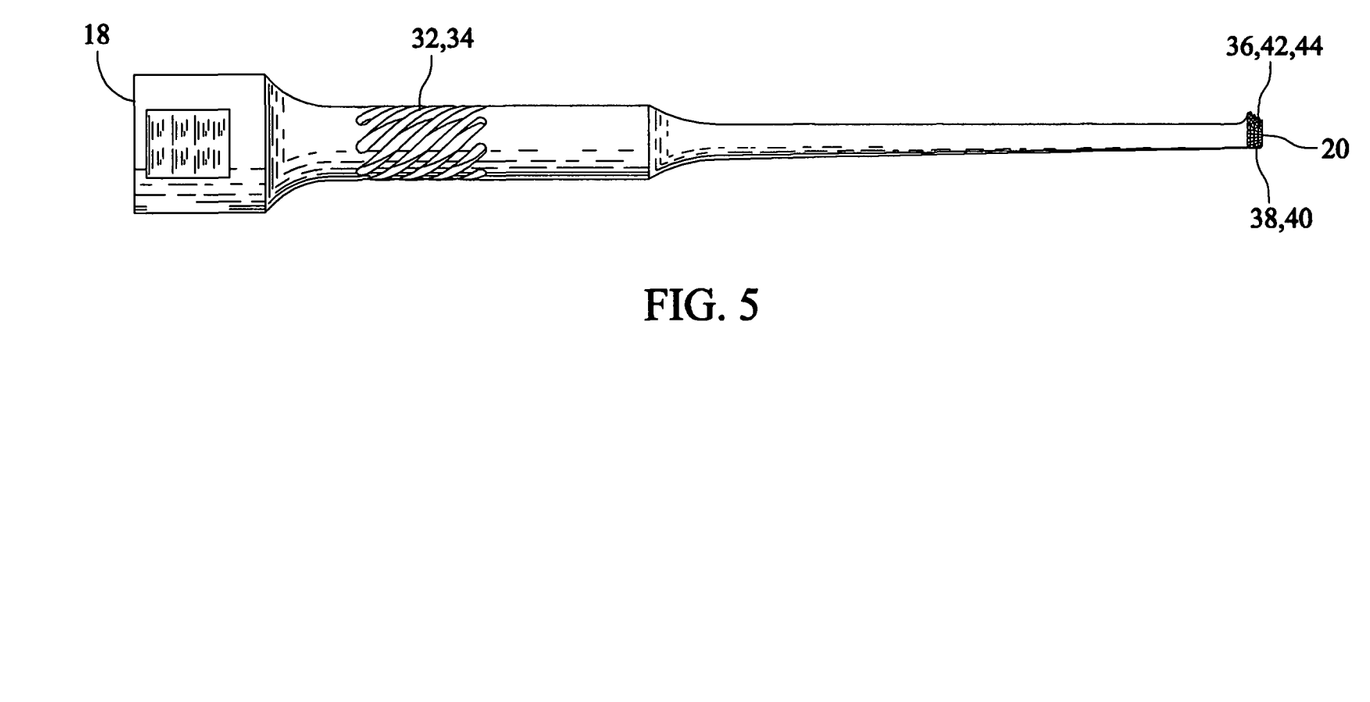
FIG. 5 is a right side plan view thereof which is substantially symmetric with a left side plan view.
Figure 6:
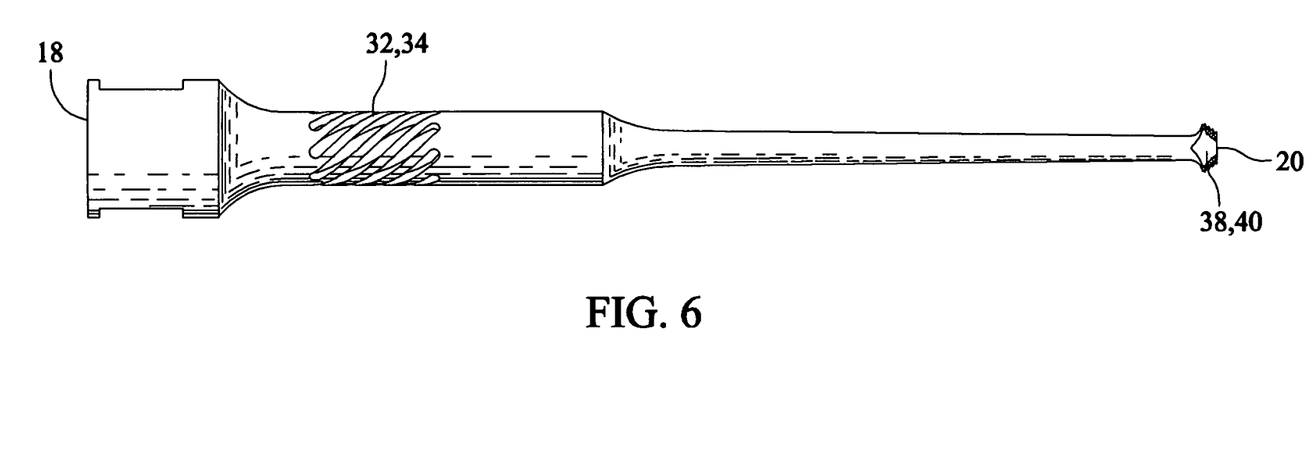
FIG. 6 is a bottom plan view thereof.
Figure 7:
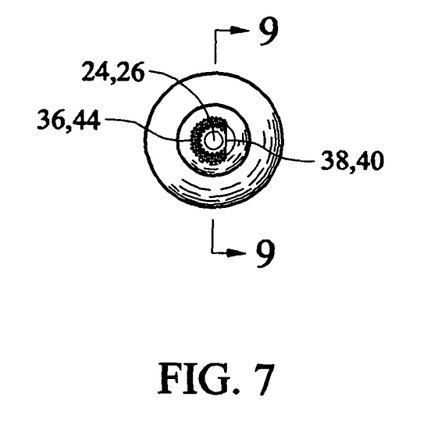
FIG. 7 is a plan front view thereof.
Figure 8:
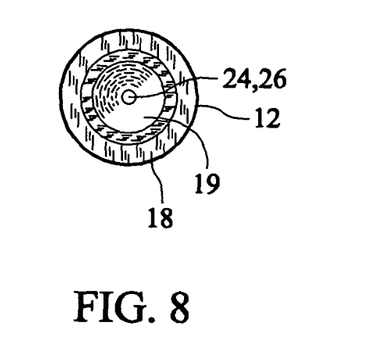
FIG. 8 is a rear plan view thereof.
Figure 9:
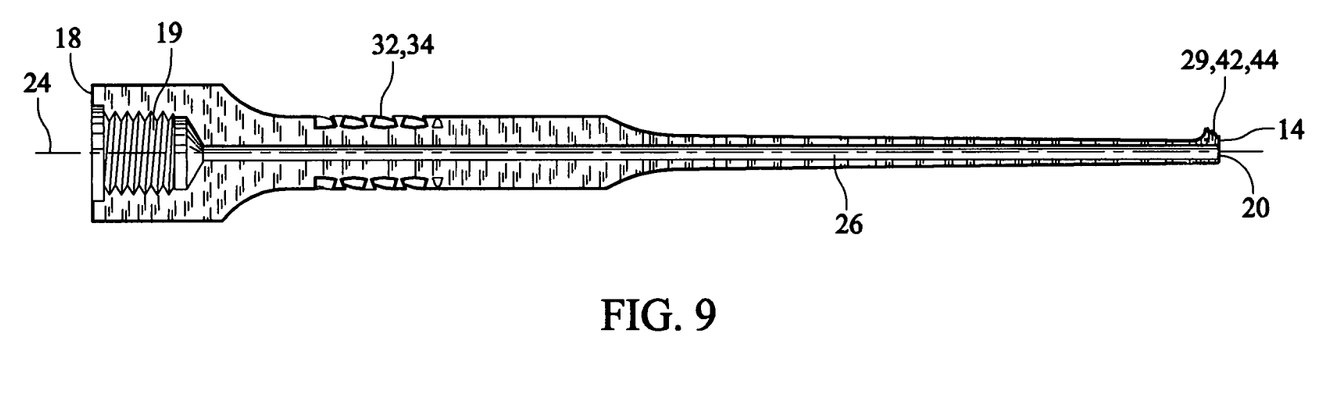
FIG. 9 is a cross sectional view thereof taken along lines 9-9 of FIG. 7.
Figure 10:
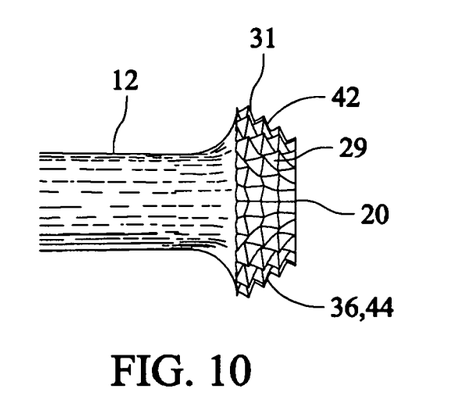
FIG. 10 is an exploded top plan view of the distal end of a preferred embodiment tip.
Figure 11:
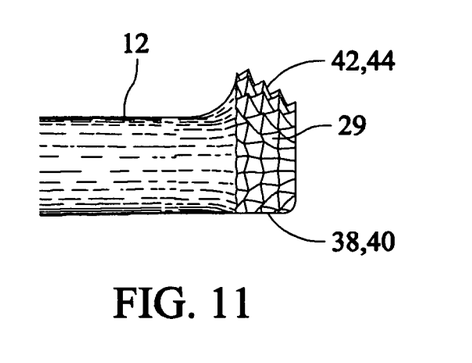
FIG. 11 is an exploded right plan view thereof of the distal end of the tip which is symmetric with a left plan view.
Figure 12:
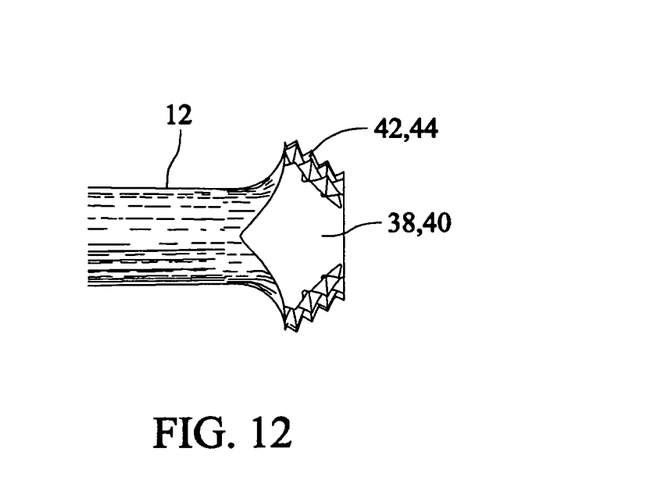
FIG. 12 is an exploded front plan view thereof of the distal end of the tip.
Figure 13:
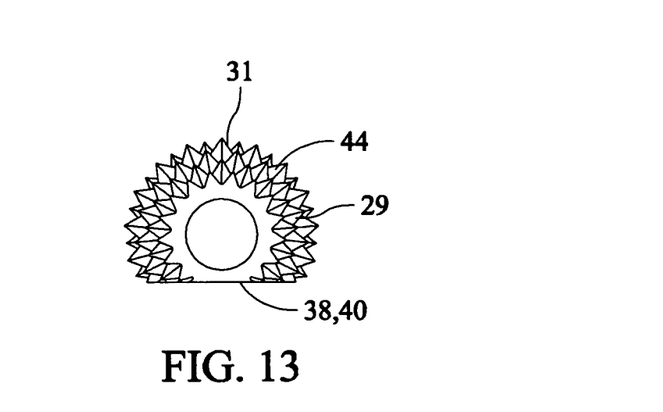
FIG. 13 is an exploded bottom plan view thereof of the distal end of the tip.
Figure 14:
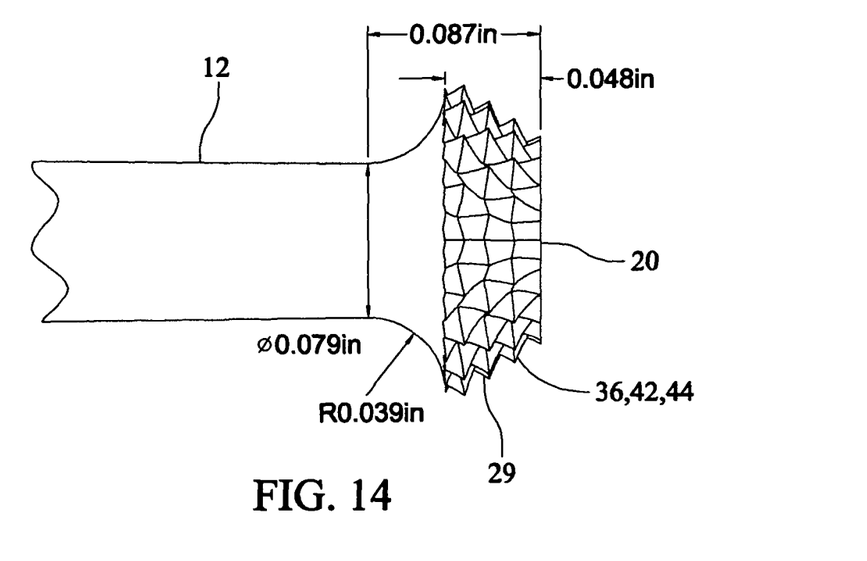
FIG. 14 another exploded top plan view of the distal end of the preferred embodiment tip with preferred dimensions.
Figure 15:
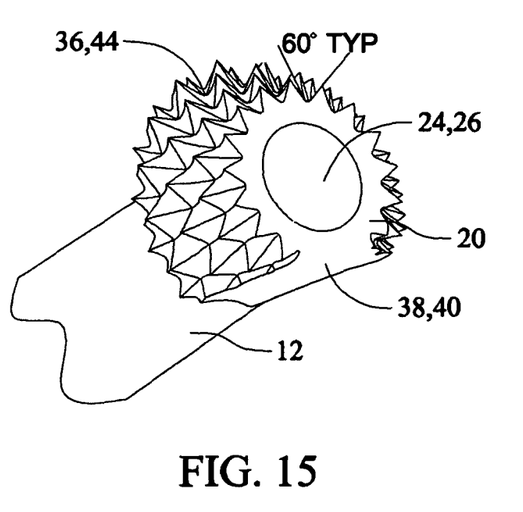
FIG. 15 is a exploded perspective view thereof of the distal end of the tip.
Figure 16:
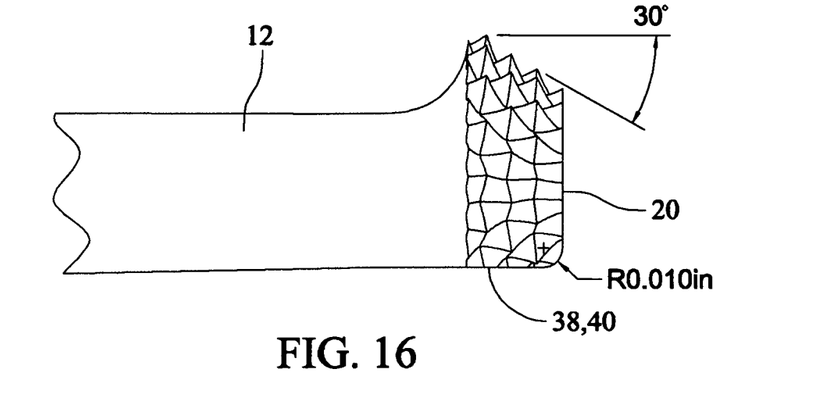
FIG. 16 is another exploded right side plan view thereof of the distal end of the tip which is symmetric with a left plan view.
Figure 17:
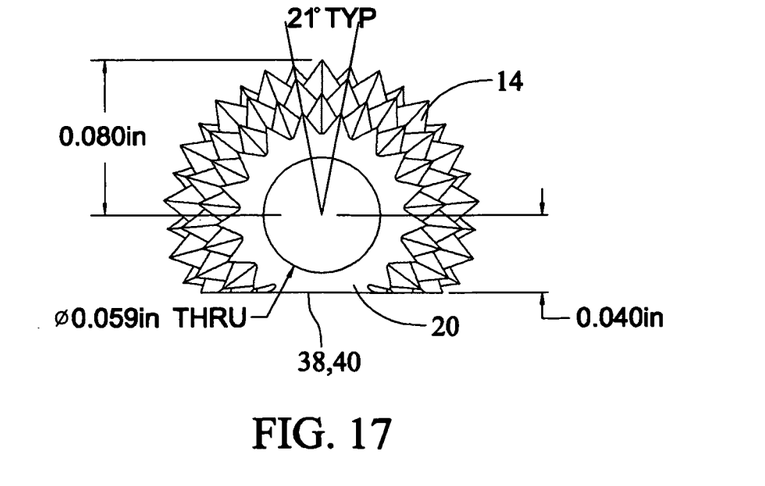
FIG. 17 another exploded front plan view thereof of the distal end of the tip.

Referring now to the drawings, there is shown in FIGS. 1-2 a prior art embodiment and in FIGS. 3-17 a preferred embodiment of a torsional dissection tip 10 having a longitudinal-torsional resonator 12 (L-T resonator) having a cutting surface tip 14 comprising a plurality of teeth 29 arranged with a pitch, i.e. distance between successive teeth 29 in a plane of motion, substantially equal to the torsional displacement of said tip 10. Said L-T resonator 12 has a first or proximal end 18 having a preferably female threaded portion 19 which connects with an ultrasonic generator or electro-mechanical transducer and a second or distal end 20 having said cutting surface plane 22. A central axis 24 of said L-T resonator 12 is centrally located and extends from said first end 18 to said second end 20. In a preferred embodiment, a tubular irrigation path 26 extends from said threaded portion 19 through said second end 20. Also in a preferred form, from said first end 18 to said second end 20 said L-T resonator 12 tapers 28 in step form 30 with preferably three steps 30. Alternative embodiments may utilize any number of steps 30 or simply taper said L-T resonator 12 and further use numerous first end 18 connecting methods recognized within the art including but not limited to screw threads, pins, press fits, welding, brazing or the connection may be metallurgically continuous with the ultrasonic generator. Said ultrasonic generator or electro-mechanical transducer is described in the prior art and is only referenced herein as it interfaces with the present invention 10.

As described within the prior art, within the body of said L-T resonator 12 is a cross sectional mass which is inhomogeneous 32. Said inhomogeneous section 32 may take the form of twisting a flat bar or grooving a round one, i.e. spiraling grooves 34 around the circumference, or varying the density or elasticity of the bar in a helical manner. This inhomogeneity 32 should preferentially be made in the portion of the bar subjected to maximum stress. When the aforesaid inhomogeneity 32 is introduced, longitudinal motion of the ultrasonic generator is at least partially converted into torsional motion at the working surface or distal tip 20. In the preferred embodiment, said inhomogeneity 32 comprises a plurality of helical grooves 34 within the second step 30 of the L-T resonator 12.

In a prior art embodiment, said cutting surface 22 plane is preferably positioned substantially tangential and away from the outside diameter of the L-T resonator 12 at said second end 20. That is, said surface 22 is preferably positioned on a short arm 23 at said second end 20 away from the outer diameter or circumference of said L-T resonator 12. Preferably said cutting surface 22 is planar 25 or has a radius 27 which substantially conforms to the radius from the central axis 24 of the L-T resonator 12 to the cutting surface 22. In said prior art embodiment said planar cutting surface 22 has substantially rectangular dimensions of 0.079 by 0.048 inch but may be of any desirable size or area. As shown in the figures, the present art uniquely incorporates a plurality of cutting teeth 29 on said cutting surface 22 which are capable of cutting hard tissue both longitudinally and torsionally. In the form described, each of said teeth 29 substantially come to a point 31 maximally away from said central axis 24. In a preferred form, said teeth 29 are pyramidal or tetrahedral in shape and uniformly positioned onto said cutting surface 22. Said teeth 29 may take substantially one dimensional triangular or rectangular, cubical, or other tetrahedral, pentahedral, or pyramidal forms with any number of surfaces in alternative embodiments.

In a preferred embodiment said cutting surface 22 is substantially partially conical 36 with a portion of the conical surface 36 removed 38 and replaced with a flat surface 40. Further alternative embodiments may utilize a full conical surface as aforedescribed without utilization of said flat 40. Said flat 40 surface represents a safe area which will not cut during operation.

In the preferred embodiment, said cutting surface 22 specifically comprises a partial conical surface 36 initially having a 0.080 inch radius relative to the central axis and tapering 42 at a 30 degree angle to a smaller radius at said distal end. Other radii and angles may be utilized in further alternative embodiments. Said surface 22 preferably consists of an expanded head 44 with pyramidal projections located circumferentially around the distal 20 shaft tubular irrigation path 26 orifice. Preferably the length of said surface as measured along the central axis 24 of the L-T resonator is approximately 0.048 inch with an actual surface length of approximately 0.055 inch but may comprise a plurality of other lengths in alternative embodiments. In the preferred embodiment, said flat 40 replacing a portion of said partially conical surface 36 is positioned 0.040 inch relative to or from said central axis 24 and represents a smooth non-cutting surface along the conical surface 36. In a preferred embodiment, said flat surface 40 is planarly parallel with said central axis 24. Also in the preferred embodiment, said surface 36 comprises four adjacent rows of teeth 29 circumferentially arranged around the surface of said partially conical surface 36, each tooth 29 at a substantially 21 degree angle relative to an adjacent row tooth 29. The pointed portion or projection of each tooth 29 of each row are preferably positioned adjacent to a trough or indented portion of the successive row teeth. Further alternative embodiments may vary this pattern and number provided the substantially conical form is retained. In the preferred alternative embodiment, the L-T resonator shaft which connects with said cutting surface 36 is approximately 0.079 inch diameter and tapers with an approximate 0.039 inch radius to said initial 0.080 inch radius of the cutting surface 36. Utilizing the aforesaid geometric form provides at least 260 degrees of cutting surface in a preferred embodiment.

Further alternative embodiments may vary the aforesaid specific geometric attributes. Specifically, said conical form 36 may be replaced with a radially conical form or pure radial form. Further alternative embodiments may vary the type, pitch, style, and location of teeth. Placement, orientation, and shape of the flat surface 40 may vary or be eliminated in alternative embodiments.

The present art invention allows the efficient removal of bone with torsional or longitudinal motion of the instrument tip 14. The device may be applied to ultrasonic motors that vibrate longitudinally, in torsion, or a combination of both longitudinal and torsional motion. That is, unlike grooves of the prior art, the present art plurality of teeth 29 will remove dense tissues when motion is applied in any two dimensional direction along the plane of the plurality of teeth 29.

As aforesaid, in the prior art embodiment, the plane of the working surface 22 is substantially parallel yet offset to the central axis of the distal tip 20 of the instrument, however the position of the working surface can be varied in a virtually limitless manner. For the preferred embodiment, the plane of the working surface is substantially partially conical 36 and offset to the central axis 24 of the distal tip 20 of the instrument, and also allows a varied positioning of the working surface in a virtually limitless manner. The plurality of pyramid shaped teeth 29 are arrayed on the working surface 22 with the pointed portions 31 farthest from said central axis.

The vibration amplitude or displacement at the working surface 22 is typically approximately 300 microns (0.3 mm) and the tooth 29 pitch is in a preferred embodiment substantially equal to said vibration amplitude. The shape of the teeth 29 and array pattern may take many forms provided the working surface provides a plurality of teeth 29. For alternative embodiments, the tooth 29 pitch should be no greater than two times the vibration amplitude and as aforesaid, in a preferred form, be equal to or less than the vibration amplitude. This allows the path swept by the vibrating teeth 29 to coincide or overlap with the path of the adjacent tooth 29. In this manner bone is removed along the entire working surface of the tip 14, disallowing the entrapment of the heat by the intimate contact of the sides of the teeth 29 with the bone. As such, heat generation is minimized, bone removal is maximized, and deleterious secondary effects are eliminated. The term "amplitude" as used herein refers to the peak displacement in a single direction as in the definition of the amplitude of a sinusoid and the term "stroke" refers to the total displacement, i.e. twice the amplitude, as in the peak-to-peak value of a sinusoid.

During operation, the unique cutting surface or head 22, 44 allows surgeon orientation of the distal end or tip with a minimal of manipulation. With the preferred embodiment, the surgeon may obtain a 360 degree angle of attack onto the target tissue with less than or equal to a 90 degree hand rotation. This unique minimization of hand manipulation is not found in prior art torsional dissection tips.

The art of the present invention may be manufactured from a plurality of materials having the elastic and hardness properties desired, including but not limited to titanium alloys, commercially pure titanium, and super-elastic alloys such as nitinol. The present art may further utilize anti-reflective surface treatments, coatings, or processes to optimize operation.

Those skilled in the art will appreciate that a torsional dissection tip 10 has been shown and described. The present invention is contemplated as effective in the removal of bone, bony prominences, calcified neoplasm, cartilage, cartilaginous materials, intervertebral disc, and other pathologies when the cutting surface 22 contacts such. The device is especially useful during neurosurgery, especially inside-out bone dissection once the superficial cortex has been removed, spinal surgery, orthopedic surgery, plastic/reconstructive surgery, and ear, nose, throat surgery, and other surgeries whereby the aforesaid tissues are encountered.

Having described the invention in detail, those skilled in the art will appreciate that modifications may be made of the invention without departing from its spirit. Therefore, it is not intended that the scope of the invention be limited to the specific embodiments illustrated and described. Rather it is intended that the scope of this invention be determined by the appended claims and their equivalents.

What is claimed is:

1. An ultrasonic dissection tip for use with an ultrasonic generator, said tip comprising:
   an ultrasonic resonator having a body, a first proximal end, a coupling feature at said first proximal end for coupling to the ultrasonic generator, and a second distal end, said second distal end capable of a torsional motion amplitude, a longitudinal motion amplitude, or a longitudinal-torsional motion amplitude when said first proximal end is excited by the ultrasonic generator producing a displacement;
   said body having three sections of decreasing outer diameter from said proximal end to said second distal end wherein said three sections include a proximal section, a distal section, and a middle section between said proximal and distal sections;
   a plurality of helical grooves formed in said middle section;
   a path extending from said proximal end to said second distal end;
   a substantially conical cutting surface adjacent said second distal end with a smallest radius of said conical cutting surface at said second distal end;
   said conical cutting surface having an arc of at least 180 degrees relative to a central axis;
   a plurality of cutting teeth having a pyramidal or tetrahedral form on said conical cutting surface; and
   said cutting teeth having a pitch less than or equal to two times at least one of said amplitudes.

2. The ultrasonic dissection tip as set forth in claim 1 wherein said conical cutting surface further comprises:
   a partially conical surface having a removed portion with a flat surface substantially planarly parallel with said central axis.

3. The ultrasonic dissection tip as set forth in claim 2 wherein said cutting teeth further comprise:
   four adjacent rows of teeth circumferentially arranged around said partially conical surface.

4. The ultrasonic dissection tip as set forth in claim 1 wherein:
   said coupling feature includes a threaded portion at said first proximal end connectable with the ultrasonic generator;
   said tubular path extends from said threaded portion through said second distal end; and
   said plurality of helical grooves are configured to convert at least a portion of the displacement from the ultrasonic generator to a torsional displacement at said second distal end.

5. The ultrasonic dissection tip as set forth in claim 4, wherein said conical cutting surface further comprises:
   an expanded head having a removed portion;
   an approximate 0.080 inch initial radius relative to said central axis and an approximate 30 degree taper toward said second distal end; and
   said removed portion representing a flat positioned approximately 0.040 inches from said central axis.

6. The ultrasonic dissection tip as set forth in claim 5, wherein said conical cutting surface provides at least 260 degrees of surface.

7. An ultrasonic dissection tip for use with an ultrasonic generator, said tip comprising:
a longitudinal-torsional resonator having a body, a first proximal end and a second distal end, said second distal end capable of a torsional motion amplitude, a longitudinal motion amplitude, or a longitudinal-torsional motion amplitude when said first proximal end is excited longitudinally by an ultrasonic generator,
said body having three sections of decreasing outer diameter including a proximal section, a distal section, and a middle section between said proximal and distal sections and an inhomogeneous cross sectional mass in the form of a plurality of spiraling grooves in said middle section;
a substantially conical cutting surface attached with said second distal end;
said conical cutting surface having a smallest radius at said second distal end and having at least a 180 degree arc;
a plurality of cutting teeth of a pyramidal or tetrahedral form on said conical cutting surface; and
said cutting teeth having a pitch less than or equal to at least one of said amplitudes.

8. The ultrasonic dissection tip as set forth in claim 7 wherein said conical cutting surface further comprises:
a partially conical surface having a removed substantially flat portion offset from a central axis.

9. The ultrasonic dissection tip as set forth in claim 8 wherein said removed portion further comprises:
a substantially flat surface positioned 0.04 inches or more from said central axis and substantially planarly parallel with said central axis.

10. The ultrasonic dissection tip as set forth in claim 9 further comprising:
a female threaded portion at said first proximal end which is connectable with the ultrasonic generator;
a tubular path extending from said threaded portion through said second distal end; and
said inhomogeneous cross sectional mass within said body of said longitudinal-torsional resonator representing a varying density in a helical manner, whereby at least a portion of displacement from the ultrasonic generator is converted to a torsional displacement at said second distal end.

11. The ultrasonic dissection tip as set forth in claim 10 further comprising:
said conical cutting surface having four adjacent rows of said cutting teeth circumferentially arranged with each of said rows positioned approximately 21 degrees relative to an adjacent row.

12. The ultrasonic dissection tip as set forth in claim 11 wherein said inhomogeneous cross sectional mass is positioned within said middle section at a position subjected to maximum longitudinal stress.

* * * * *

UNITED STATES PATENT AND TRADEMARK OFFICE
CERTIFICATE OF CORRECTION

| | | |
|---|---|---|
| PATENT NO. | : 8,512,340 B2 | Page 1 of 1 |
| APPLICATION NO. | : 11/174046 | |
| DATED | : August 20, 2013 | |
| INVENTOR(S) | : Easley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1920 days.

Signed and Sealed this
Twenty-seventh Day of January, 2015

Michelle K. Lee
*Deputy Director of the United States Patent and Trademark Office*